(12) United States Patent
Brown

(10) Patent No.: US 6,494,205 B1
(45) Date of Patent: Dec. 17, 2002

(54) NASAL INSERT FILTERING DEVICE

(76) Inventor: Jerry L. Brown, 933 Mc Kinley Ave., Akron, OH (US) 44306

( * ) Notice: Subject to any disclaimer, the term of this patent is extended or adjusted under 35 U.S.C. 154(b) by 0 days.

(21) Appl. No.: 09/928,081

(22) Filed: Aug. 10, 2001

(51) Int. Cl.$^7$ .............................................. A61G 10/00
(52) U.S. Cl. ............................ 128/206.11; 128/204.12
(58) Field of Search ....................... 128/203.22, 204.12, 128/204.13, 206.11

(56) References Cited

U.S. PATENT DOCUMENTS

| | | | | |
|---|---|---|---|---|
| 480,505 A | * | 8/1892 | Midgley et al. ........ | 128/204.13 |
| 611,478 A | * | 9/1898 | Hannon et al. ........ | 128/203.22 |
| 878,223 A | | 2/1908 | Meisselbach | |
| 907,178 A | * | 12/1908 | Riggs ..................... | 128/203.22 |
| 1,071,015 A | * | 8/1913 | Adler ..................... | 128/206.11 |
| 1,160,797 A | * | 11/1915 | Wallin ................... | 128/203.22 |
| 1,311,461 A | | 7/1919 | Reynard | |
| 1,474,710 A | * | 11/1923 | Grier ..................... | 128/203.22 |
| 1,950,926 A | * | 3/1934 | Lobl ..................... | 128/203.22 |
| 2,097,846 A | * | 11/1937 | Strauch ................. | 128/204.13 |
| 2,277,390 A | * | 3/1942 | Crespo ................. | 128/204.12 |
| 2,433,565 A | * | 12/1947 | Korman ................ | 128/204.12 |
| 2,715,401 A | * | 8/1955 | Appel ................... | 128/206.11 |
| 3,457,917 A | | 7/1969 | Mercurio | |
| 3,463,149 A | | 8/1969 | Albu | |
| 3,722,509 A | * | 3/1973 | Nebel ................... | 128/204.12 |
| 4,052,983 A | * | 10/1977 | Bovender ............. | 128/204.12 |
| 4,221,217 A | | 9/1980 | Amezcua | |
| 4,267,831 A | * | 5/1981 | Aguilar ................. | 128/203.22 |
| 4,401,117 A | * | 8/1983 | Gershuny .............. | 128/203.22 |
| 4,887,597 A | | 12/1989 | Holland | |
| 4,984,302 A | * | 1/1991 | Lincoln ................. | 128/204.12 |
| 5,117,820 A | * | 6/1992 | Robitaille ............. | 128/203.22 |
| 5,417,205 A | | 5/1995 | Wang | |
| 5,568,808 A | * | 10/1996 | Rimkus ................. | 128/204.12 |
| 6,216,694 B1 | * | 4/2001 | Chen .................... | 128/206.11 |

\* cited by examiner

Primary Examiner—Aaron J. Lewis

(57) ABSTRACT

A nasal insert filtering assembly for filtering impurities in an airflow flowing through the nasal passages of a user. The nasal insert filtering assembly includes a pair of housings. Each of the housings includes an interior. A filtering means is mounted in the interior of each of the housings for filtering an airflow flowing through interior of each of the housings.

10 Claims, 1 Drawing Sheet

NASAL INSERT FILTERING DEVICE

BACKGROUND OF THE INVENTION

1. Field of the Invention

The present invention relates to filters and more particularly pertains to a new nasal insert filtering assembly for filtering impurities in an airflow flowing through the nasal passages of a user.

2. Description of the Prior Art

The use of filters is known in the prior art. More specifically, filters heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 4,887,597; U.S. Pat. No. 5,147,205; U.S. Pat. No. 4,221,217; U.S. Pat. No. 3,457,917; U.S. Pat. No. 3,463,149; U.S. Pat. No. 1,311,461; and U.S. Pat. No. 878,223.

While these devices fulfill their respective, particular objectives and requirements, the aforementioned patents do not disclose a new nasal insert filtering assembly. The inventive device includes a pair of housings. Each of the housings includes an interior. A filtering means is mounted in the interior of each of the housings for filtering an airflow flowing through interior of each of the housings.

In these respects, the nasal insert filtering assembly according to the present invention substantially departs from the conventional concepts and designs of the prior art, and in so doing provides an apparatus primarily developed for the purpose of filtering impurities in an airflow flowing through the nasal passages of a user.

SUMMARY OF THE INVENTION

In view of the foregoing disadvantages inherent in the known types of filters now present in the prior art, the present invention provides a new nasal insert filtering assembly construction wherein the same can be utilized for filtering impurities in an airflow flowing through the nasal passages of a user.

The general purpose of the present invention, which will be described subsequently in greater detail, is to provide a new nasal insert filtering assembly apparatus and method which has many of the advantages of the filters mentioned heretofore and many novel features that result in a new nasal insert filtering assembly which is not anticipated, rendered obvious, suggested, or even implied by any of the prior art filters, either alone or in any combination thereof.

To attain this, the present invention generally comprises includes a pair of housings. Each of the housings includes an interior. A filtering means is mounted in the interior of each of the housings for filtering an airflow flowing through interior of each of the housings.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new nasal insert filtering assembly apparatus and method which has many of the advantages of the filters mentioned heretofore and many novel features that result in a new nasal insert filtering assembly which is not anticipated, rendered obvious, suggested, or even implied by any of the prior art filters, either alone or in any combination thereof.

It is another object of the present invention to provide a new nasal insert filtering assembly which may be easily and efficiently manufactured and marketed.

It is a further object of the present invention to provide a new nasal insert filtering assembly which is of a durable and reliable construction.

An even further object of the present invention is to provide a new nasal insert filtering assembly which is susceptible of a low cost of manufacture with regard to both materials and labor, and which accordingly is then susceptible of low prices of sale to the consuming public, thereby making such nasal insert filtering assembly economically available to the buying public.

Still yet another object of the present invention is to provide a new nasal insert filtering assembly which provides in the apparatuses and methods of the prior art some of the advantages thereof, while simultaneously overcoming some of the disadvantages normally associated therewith.

Still another object of the present invention is to provide a new nasal insert filtering assembly for filtering impurities in an airflow flowing through the nasal passages of a user.

Yet another object of the present invention is to provide a new nasal insert filtering assembly which includes a pair of housings. Each of the housings includes an interior. A filtering means is mounted in the interior of each of the housings for filtering an airflow flowing through interior of each of the housings.

Still yet another object of the present invention is to provide a new nasal insert filtering assembly that unlike the prior art may employ a plurality of filters to provide additional filtering of an airflow entering the nasal passages of a user.

Even still another object of the present invention is to provide a new nasal insert filtering assembly that is more comfortable by permitting a user to use a filter for breathing without having to wear a large mask.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
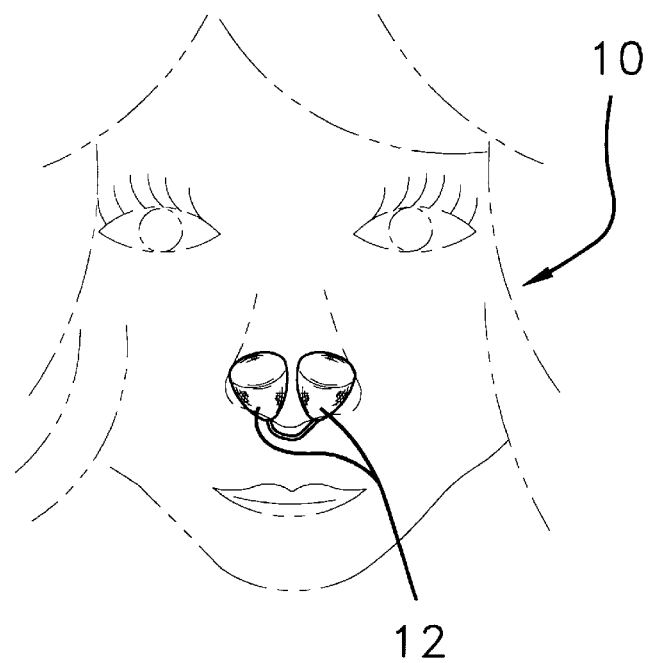
FIG. 1 is a schematic perspective view of a new nasal insert filtering assembly according to the present invention.
Figure 2:
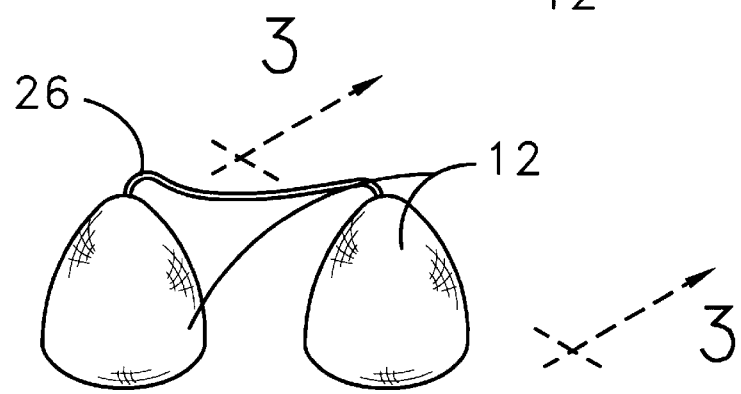
FIG. 2 is a schematic perspective view of the present invention.
Figure 3:
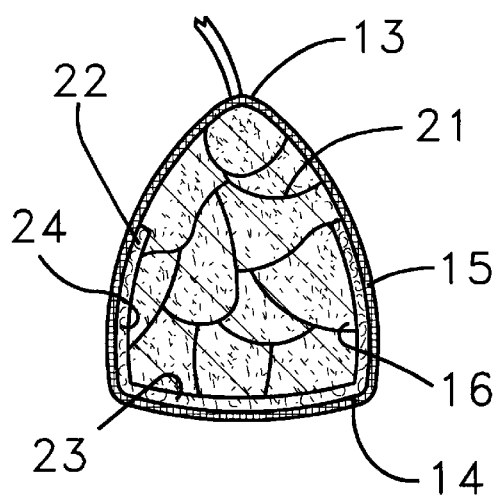
FIG. 3 is a schematic cross-sectional view of the present invention taken along line 3—3 of FIG. 2.

With reference now to the drawings, and in particular to FIGS. 1 through 3 thereof, a new nasal insert filtering assembly embodying the principles and concepts of the present invention and generally designated by the reference numeral 10 will be described.

As best illustrated in FIGS. 1 through 3, the nasal insert filtering assembly 10 generally comprises a pair of housings 12. The housings 12 include a first end 13, a second end 14 opposite the first end 13 and a peripheral wall 15 extending between the first 13 and second 14 ends defining an interior 16 of each of the housings 12.

As illustrated in FIGS. 1 and 2, the housings 12 are generally conical such that the first end 13 of each of the housings 12 are generally pointed and the second end 14 of the housings 12 are generally flat. The housings 12 may employ other shapes such as, for example a circular shape.

The housings 12 preferably comprise a generally flexible porous material to allow an airflow to flow through the housings 12. Each of the housings 12 may comprise a fabric material. The fabric material may have a plurality of colors. The different colors permit users of different colored skin to use the nasal insert filtering assembly 10 inconspicuously.

A filtering means 21 is provided for filtering the impurities in the airflow entering the interior 16 of the housings 12 by flowing through the second end 14 of each of the housings 12. The filtering means 21 is preferably mounted in the interior 16 of the housings 12.

The filtering means 21 may comprise charcoal granules. However, any type of filtering means capable of filtering impurities in an airflow may be employed.

A filtering member 22 may be provided for filtering a filtering means residue from an airflow flowing out of the filtering means 21 and before it flows out of the second end 14 of each of the housings 12. The filtering member 22 may include a base panel 23 that is positioned between the filtering means 21 and the second end 14 of the housings 12. A perimeter panel 24 may extend approximately half a length of the housing measured from the second end 14 of the housings 12 toward the first end 13 of the housings 12. In one embodiment of the present invention, as particularly illustrated in FIG. 3, the first end 13 of the housings 12 abut the filtering means 21 providing increased airflow into the interior 16 of the housings 12.

The filtering member 22 preferably comprises a generally porous material such as, for example, a cotton or fabric material. However, any type of material capable of filtering an airflow may be employed.

The nasal insert filtering assembly 10 may also include a coupling member 26 for coupling the housings 12 together and for removing each of the housings 12 from the pair of nasal passages of the user. The coupling member 26 is coupled to and extending between the first end 13 of each of the housings 12. A central portion of the coupling member 26 extends out of each of the nasal passages when each of the housings 12 is removable inserted in the nasal passages of the user. In one embodiment of the present invention, a user may remove the housings 12 by pulling on the central portion of the coupling member 26. The coupling member 26 may comprise a generally elastic material.

In use, the second end 14 of the housings 12 are placed adjacent to the nasal passages of a user. The user selectively exerts pressure against the first end 13 of the housings 12 to position the housings 12 in the nasal passages of the user. An airflow entering the first end 13 of the housings 12 flows through the filtering means 21 and then through the filtering member 22. After the airflow flows through the filtering means 21 and the filtering member 22 it flows out of the second end 14 of the housings and travels to the lungs of the user.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A nasal insert filtering assembly removably insertable in a pair of nasal passages of a user for filtering impurities in an airflow flowing through the nasal passages of the user, said assembly comprising:

a pair of housing, each of said housing having an interior; and a filtering means for filtering an airflow through the interior of the housing, said filtering means being mounted in said interior of each of said housings;

a coupling member for coupling each of said housings together and for removing each of said housings from the pair of nasal passages of the user, said coupling member being coupled to and extending between said first end of each of said housings, a central portion of said coupling member extending out of each of the nasal passages when each of said housings is removably inserted in the nasal passages of the user, where in a user removes each of said housings by pulling on said coupling member.

2. The nasal insert filtering assembly of claim 1, wherein each of said housings has a first end, a second end opposite said first end and a peripheral wall extending between said first and second ends defining said interior of each of said housings.

3. The nasal insert filtering assembly of claim 2, wherein each of said housings is generally conical such that said first end of each of said housings being generally pointed and said second end of each of said housings being generally flat, wherein a user places said second end of one of said housings in one of the pair of nasal passages and selectively exerts pressure against said first end of said housing to position said housing in the nasal passages of the user.

4. The nasal insert filtering assembly of claim 1, wherein each of said housings comprises a generally flexible porous material.

5. The nasal insert filtering assembly of claim 1, wherein said filtering means comprises charcoal granules.

6. The nasal insert filtering assembly of claim 1, additionally including a filtering member for filtering a filtering means residue from an airflow flowing out of said filtering means and before the airflow flows out of said second end of each of said housings, said filtering member having a base panel being positioned between said filtering means and said second end of each of said housings.

7. The nasal insert filtering assembly of claim 6, additionally including a perimeter panel extending approximately half a length of each of said housings measured from said second end to said first end, wherein said first end of each of said housings abuts said filtering means.

8. The nasal insert filtering assembly of claim 6, wherein said filtering member comprises a generally porous material.

9. The nasal insert filtering assembly of claim 1, wherein said coupling member comprises a generally elastic material.

10. A nasal insert filtering assembly removably insertable in a pair of nasal passages of a user for filtering impurities from an airflow flowing through the nasal passages of the user, said assembly comprising:

a pair of housings, each of said housings having a first end, a second end opposite said first end and a peripheral wall extending between said first and second ends defining an interior of each of said housings;

each of said housings being generally conical such that said first end of said housing being generally pointed and said second end of said housing being generally flat, wherein a user places said second end of one of said housings in one of the pair of nasal passages and selectively exerts pressure against said first end of said housing to position said housing in the nasal passages of the user;

said housing comprising a generally flexible porous material;

a filtering means for filtering the impurities from an airflow entering the nasal passages of the user and entering said interior of said housings by flowing through said first end of said housings, said filtering means being mounted in said interior of said housings;

said filtering means comprising charcoal granules;

a filtering member for filtering a filtering means residue from an airflow flowing out of said filtering means before the airflow flows out of said second end of said housing, said filtering member having a base panel being positioned between said filtering means and said second end of said housing, a perimeter panel extending approximately half a length of said housing measured from said second end to said first end, wherein said first end of said housing abuts said filtering means;

said filtering member comprising a generally porous material;

said filtering member comprising cotton;

a coupling member for coupling each of said housings together and for removing each of said housings from the pair of nasal passages of the user, said coupling member being coupled to and extending between said first end of each of said housings, a central portion of said coupling member extending out of each of the nasal passages when each of said housings is removably inserted in the nasal passages of the user, wherein a user removes each of said housings by pulling on said coupling member; and said coupling member comprising a generally elastic material.

\* \* \* \* \*